(12) United States Patent
Chirila et al.

(10) Patent No.: US 12,601,750 B2
(45) Date of Patent: Apr. 14, 2026

(54) DIAGNOSING MILD COGNITIVE IMPAIRMENT (MCI), PREDICTING ALZHEIMER'S DISEASE (AD) DEMENTIA ONSET, AND SCREENING AND MONITORING AGENTS FOR TREATING MCI OR PREVENTING DEMENTIA ONSET

(71) Applicant: WEST VIRGINIA UNIVERSITY, Morgantown, WV (US)

(72) Inventors: Florin V. Chirila, Morgantown, WV (US); Daniel L. Alkon, Chevy Chase, MD (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 0 days.

(21) Appl. No.: 18/763,515

(22) Filed: Jul. 3, 2024

(65) Prior Publication Data

US 2024/0353429 A1      Oct. 24, 2024

Related U.S. Application Data

(63) Continuation of application No. 16/077,766, filed as application No. PCT/US2017/018810 on Feb. 22, 2017, now abandoned.

(60) Provisional application No. 62/298,182, filed on Feb. 22, 2016.

(51) Int. Cl.
*G01N 33/68* (2006.01)
*G16H 50/20* (2018.01)

(52) U.S. Cl.
CPC ......... *G01N 33/6896* (2013.01); *G16H 50/20* (2018.01); *G01N 2800/2821* (2013.01); *G01N 2800/60* (2013.01)

(58) Field of Classification Search
CPC ....... G01N 33/6896; G01N 2800/2821; G01N 2800/60; G16H 50/20; G16B 5/00
See application file for complete search history.

(56) References Cited

U.S. PATENT DOCUMENTS

| 2012/0141498 A1 | 6/2012 | Acevedo-Duncan |
| 2014/0038186 A1 | 2/2014 | Khan |

FOREIGN PATENT DOCUMENTS

| JP | 2013506844 A | 2/2013 |
| JP | 2013520652 A | 6/2013 |
| WO | 2011041670 A2 | 4/2011 |
| WO | 2015103495 A1 | 7/2015 |

OTHER PUBLICATIONS

David S. Knopman, Md, et al., "Mild Cognitive Impairment and Mild Dementia: A Clinical Perspective," 2014 Mayo Foundation for Medical Education and Research, Oct. 2014, pp. 1452-1459, May Col Proc. 2014: 89(10)1452-1459.
Tapan K. Khan, et al., "PKC[Epsilon] Deficits in Alzheimer's Disease Brains and Skin Fibroblasts," Journal of Alzheimer's Disease 43, Jun. 16, 2014, pp. 491-509.
Florin V. Chirila et al., "Spatiotemporal Complexity of Fibroblast Networks Screens for Alzheimer's Disease," Journal of Alzheimer's Disease 33 (2013), pp. 165-176.
Florin V. Chirila, et al., "Fibroblast Aggregation Rate Converges with Validated Peripheral Biomarkers for Alzheimer's Disease," Journal of Alzheimer's Disease 42 (Jul. 2014) pp. 1279-1294.
European Office Action re 17/712,270.2-1110 dated Apr. 8, 2021, 7 pgs.
Translation of Office Action dated Dec. 21, 2020 re Patent Application No. 2018-563394.
International Search Report & Written Opinion dated Jun. 8, 2017 for PCT/US2017/011810.

*Primary Examiner* — Olga N Chernyshev
(74) *Attorney, Agent, or Firm* — Kramer & Amado, P.C.

(57) ABSTRACT

Methods of detecting the signature of Alzheimer's disease before the clinical onset of the disease are disclosed, such as methods of diagnosing Mild Cognitive Impairment (MCI), monitoring the progress of MCI, and predicting the time to clinical onset of AD dementia. The methods use a Biomarker Severity Score, which corresponds to output signals of one or more biomarkers chosen from AD Index, Morphometric Imaging, and PKC Epsilon Biomarkers. Also disclosed are methods of screening for a compound useful for treating MCI or for preventing the clinical onset of AD dementia, as well as methods of evaluating or monitoring the therapeutic benefit of an agent for treating MCI or preventing the clinical onset of AD dementia.

9 Claims, 10 Drawing Sheets

MORPHOMETRIC IMAGING BIOMARKER

PKCe BIOMARKER

MORPHOMETRIC IMAGING BIOMARKER

PKCe BIOMARKER
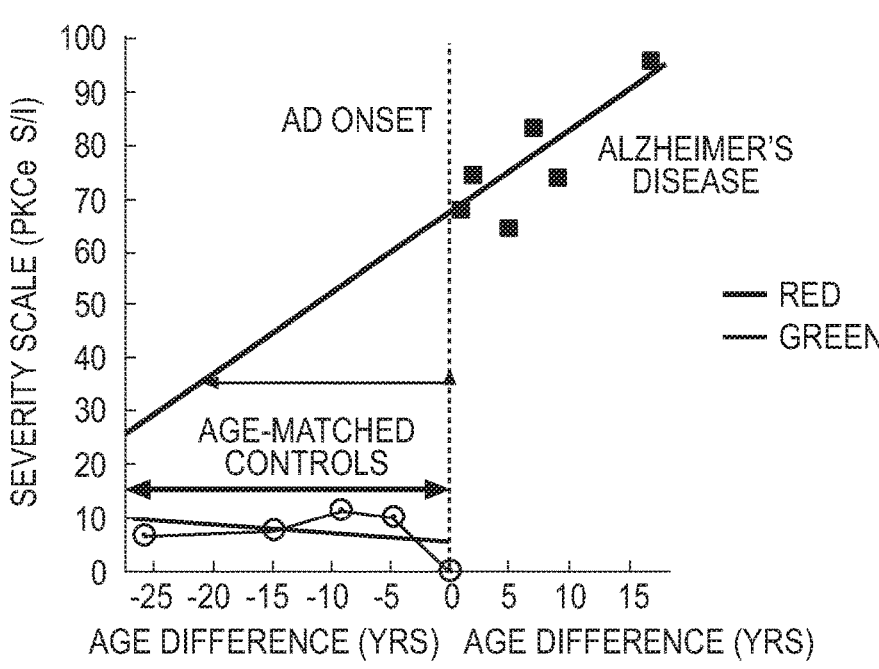
FIG. 5B
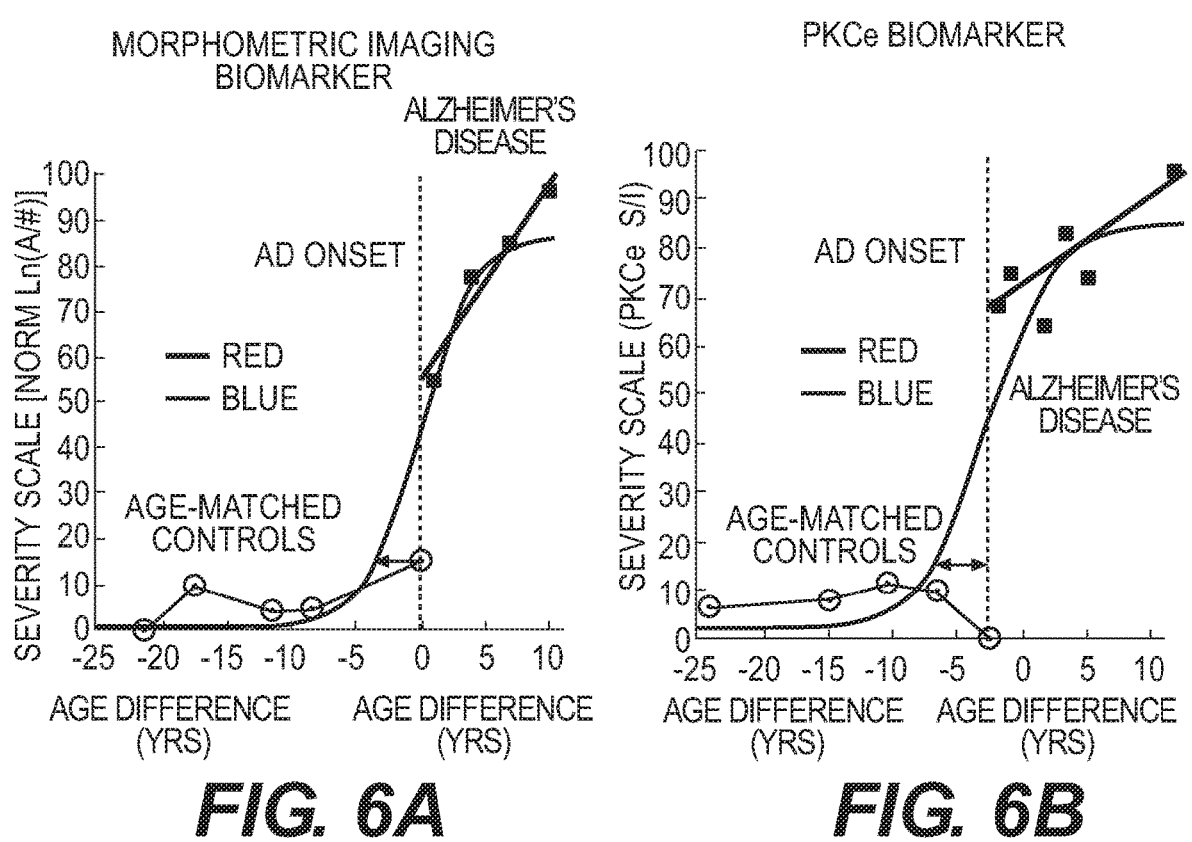
FIG. 6A          FIG. 6B

DIAGNOSING MILD COGNITIVE IMPAIRMENT (MCI), PREDICTING ALZHEIMER'S DISEASE (AD) DEMENTIA ONSET, AND SCREENING AND MONITORING AGENTS FOR TREATING MCI OR PREVENTING DEMENTIA ONSET

This application is a continuation of U.S. Ser. No. 16/077,766, filed Aug. 14, 2018, which is a § 371 national stage entry of PCT Application No. PCT/US2017/018810, filed Feb. 22, 2017, which claims priority to U.S. Provisional Application 62/298,182, filed Feb. 22, 2016, the entire contents of all of which are incorporated herein by reference.

Alzheimer's disease (AD) is a neurodegenerative disorder generally characterized by the progressive decline of mental functioning. More specifically, AD is characterized clinically by the progressive loss of memory, cognition, reasoning, judgment, and emotional stability that gradually leads to profound mental deterioration and, ultimately, death. Although there are many hypotheses for the possible mechanisms of AD, one central theory is that the excessive formation and accumulation of toxic beta-amyloid (AB) peptides either directly or indirectly affects a variety of cellular events and leads to neuronal damage and cell death.

AD is a progressive disorder with a mean duration of around 8-15 years between onset of clinical symptoms and death. AD is believed to represent the seventh most common medical cause of death and affects about 5 million people in the United States.

The value of diagnostic biomarkers derives from their ability to monitor disease progression and remission, as well as their predictive accuracy before the onset of the disease. Detection of AD even before its onset, could provide important opportunities for prevention and/or planning therapeutic strategies. For example, Mild Cognitive Impairment has been characterized as a decline in cognition that is greater than the level expected for an individual's age and education level but that does not interfere notably with activities of daily life. It represents an intermediate stage between the expected cognitive changes of normal aging and the earliest clinical manifestations of dementia. MCI increases the risk of developing Alzheimer disease. In the early stages of AD, however, within four years from the dementia onset, clinical diagnosis has a limited rate of success. Furthermore, clinical diagnostic accuracy before dementia onset has not been previously validated. Thus, there is a need to develop improved diagnostic and predictive capabilities for AD. In particular, there is a need to develop methods to detect the signature of AD before the clinical onset of dementia.

The methods of the present disclosure address these needs by providing for methods of diagnosing MCI, of monitoring the progression of MCI, and of predicting the time to clinical onset of AD dementia. The present disclosure is also directed to methods of screening for a compound useful for treating MCI or for preventing the clinical onset of AD dementia, as well as methods of evaluating or monitoring the therapeutic benefit of an agent for treating MCI or preventing the clinical onset of AD dementia.

In one aspect of the present disclosure, a method of diagnosing MCI in a subject comprises:

(a) obtaining one or more cells from the subject;

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker; and (c) comparing the output signal determined in step (b) to output signals of the diagnostic biomarker for age-matched control (AC) cells and for AD cells, wherein MCI is indicated in the subject if the output signal determined in step (b) is less than the lowest output signal for the AD cells but greater than the highest output signal for the AC cells.

In another aspect, a method of monitoring the progression of MCI in a subject comprises:

(a) obtaining one or more cells from the subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker:

(c) comparing the output signal determined in step (b) to output signals of the diagnostic biomarker for AC cells and for AD cells, wherein MCI is indicated in the subject if the output signal determined in step (b) is less than the lowest output signal for the AD cells but greater than the highest output signal for the AC cells; and (d) repeating steps (a) through (c) at one or more subsequent points in time, wherein the subject has progressed toward the clinical onset of AD dementia if the output signals determined in step (b) have increased over time.

In another aspect, a method of predicting the time to clinical onset of AD dementia in a subject comprises:

(a) obtaining one or more cells from the subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker:

(c) comparing the output signal determined in step (b) to output signals of the diagnostic biomarker for AC cells from a group of AC subjects and to output signals of the diagnostic biomarker for AD cells from a group of AD subjects, wherein MCI is indicated in the subject if the output signal determined in step (b) is less than the lowest output signal for the AD cells but greater than the highest output signal for the AC cells:

(d) plotting the output signals of the diagnostic biomarker for the AD cells as a function of their AD duration, wherein each AD duration is the age difference between the AD subject's age at the time of clinical onset of AD and the AD subject's age at the time of collecting one or more cells for generating the output signals of the diagnostic biomarker:

(e) fitting a function to the plotted output signals of step (d); and (f) if MCI is indicated in step (c), predicting the time to clinical onset of AD dementia by inputting into the fit function the output signal of the diagnostic biomarker determined in step (b) and determining the time to clinical onset of AD dementia.

In another aspect, a method of predicting the time to clinical onset of AD dementia in a subject comprises:

(a) obtaining one or more cells from the subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker:

(c) comparing the output signal determined in step (b) to output signals of the diagnostic biomarker for AC cells from a group of AC subjects and to output signals of the diagnostic biomarker for AD cells from a group of AD subjects, wherein MCI is indicated in the subject if the output signal determined in step (b) is less than the lowest output signal for the AD cells but greater than the highest output signal for the AC cells:

(d) plotting the output signals of the diagnostic biomarker for the AD cells as a function of their AD duration, wherein each AD duration is the age difference between an AD subject's age at the time of clinical onset of AD and the AD subject's age at the time of collecting one or more cells for generating the output signals of the diagnostic biomarker;

(e) plotting the output signals of the diagnostic biomarker for the AC cells as a function of their age difference, wherein each age difference is the difference between an AC subject's age at the time of collecting one or more cells for generating the output signals of the diagnostic biomarker and the age of the oldest AC subject at the time of collecting one or more cells for generating the output signals of the diagnostic biomarker:

(f) fitting a function to the plotted output signals of steps (d) and (e); and (g) if MCI is indicated in step (c), predicting the time to clinical onset of AD dementia by inputting into the fit function the output signal of the diagnostic biomarker determined in step (b) and determining the time to clinical onset of AD dementia.

In another aspect, a method of screening for a compound useful for treating MCI or preventing the clinical onset of AD dementia comprises:

(a) obtaining one or more cells from a subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker;

(c) comparing the output signal determined in step (b) to output signals of the diagnostic biomarker for AC cells and for AD cells, wherein MCI is indicated in the subject if the output signal determined in step (b) is less than the lowest output signal for the AD cells but greater than the highest output signal for the AC cells:

(d) if MCI is indicated in step (c), determining the output signal of the diagnostic biomarker in step (b) after contacting cells from the subject with a compound for an initial time period and/or for an ongoing time period; and (e) comparing the output signal determined in step (d) to the output signal determined in step (b), wherein the test compound is indicated as useful for the treatment of MCI or the prevention of the clinical onset of AD dementia if the output signal determined in step (d) is less than the output signal determined in step (b).

In another aspect, a method of evaluating or monitoring the therapeutic benefit of an agent for treating MCI or preventing the clinical onset of AD dementia in a subject comprises:

(a) obtaining one or more cells from a subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker:

(c) comparing the output signal determined in step (b) to output signals of the diagnostic biomarker for AC cells and for AD cells, wherein MCI is indicated in the subject if the output signal determined in step (b) is less than the lowest output signal for the AD cells but greater than the highest output signal for the AC cells;

(d) if MCI is indicated in step (c), determining the output signal of the diagnostic biomarker in step (b) using one or more cells from the subject after initial, ongoing, and/or cessation of treatment with an agent; and (e) comparing the output signal determined in step (d) to the output signal determined in step (b), wherein the agent is indicated as providing therapeutic benefit for treating MCI or preventing the clinical onset of AD dementia in the subject if the output signal determined in step (d) is equal to or less than the output signal determined in step (b).

BRIEF DESCRIPTION OF THE FIGURES

FIG. 1A shows the total number of synapses$\times 10^{10}$ in the outer molecular layer of the hippocampal dentate gyrus (closed triangles and the left y-scale) and the MMSE score (open triangles and the right y-scale). FIG. 1B uses the same values as in FIG. 1A and scales them between 0 and 100, showing a severity score for total number of synapses and the MMSE score. The curves are the best-fit logistic functions.

FIG. 3A plots the output signals of the Morphometric Imaging Biomarker as a function of AD duration (The minimum and maximum values for Ln (A/N) were scaled between 0 and 100) and FIG. 3B plots the output signals of the PKC Epsilon Biomarker as a function of AD duration (The minimum and maximum values for S/I were called between 0 and 100.). Each plot includes a linear fit line.

FIG. 5B is similar to FIG. 4B but further illustrates the predictive value of the PKC Epsilon Biomarker following the linear dependence of the AD group.

FIGS. 6A, 6B, and 6C illustrate the predictive value of the Morphometric, PKC Epsilon, and AD Index Biomarkers, respectively, applying a logistic fit function rather than linear.

DESCRIPTION

As used herein, the singular forms "a," "an," and "the" include plural reference.

As used herein, "protein kinase C activator" or "PKC activator" refers to a substance that increases the rate of the reaction catalyzed by PKC. PKC activators can be non-specific or specific activators. A specific activator activates one PKC isoform, e.g., PKC-E (epsilon), to a greater detectable extent than another PKC isoform.

The term "subject" or "subjects" used herein is non-limiting. It refers to humans, but can also include other mammals, such as mice, rats, monkeys, and apes.

Figure 1A:
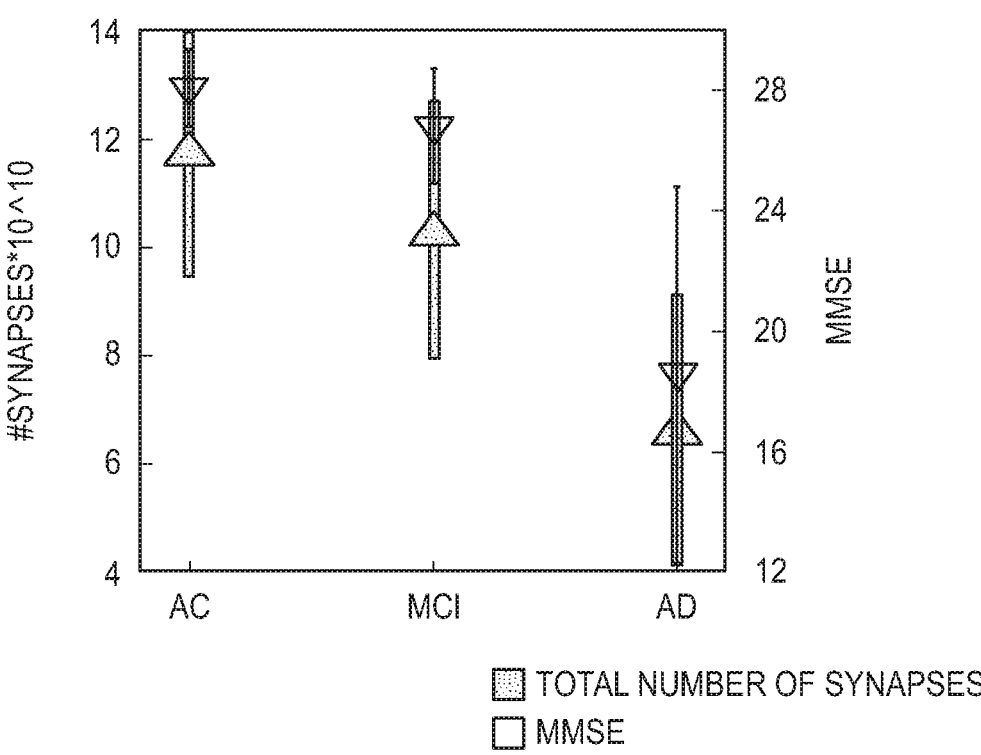
FIGS. 1A and 1B show a correlation between the loss of synapses and the Mini-Mental State Examination (MMSE) score in MCI patients based on the average of the total number of synapses in the outer molecular layer of the hippocampal dentate gyrus and the average MMSE score for three populations: Age-matched controls (AC), MCI patients, and AD patients. In particular.
Figure 1B:
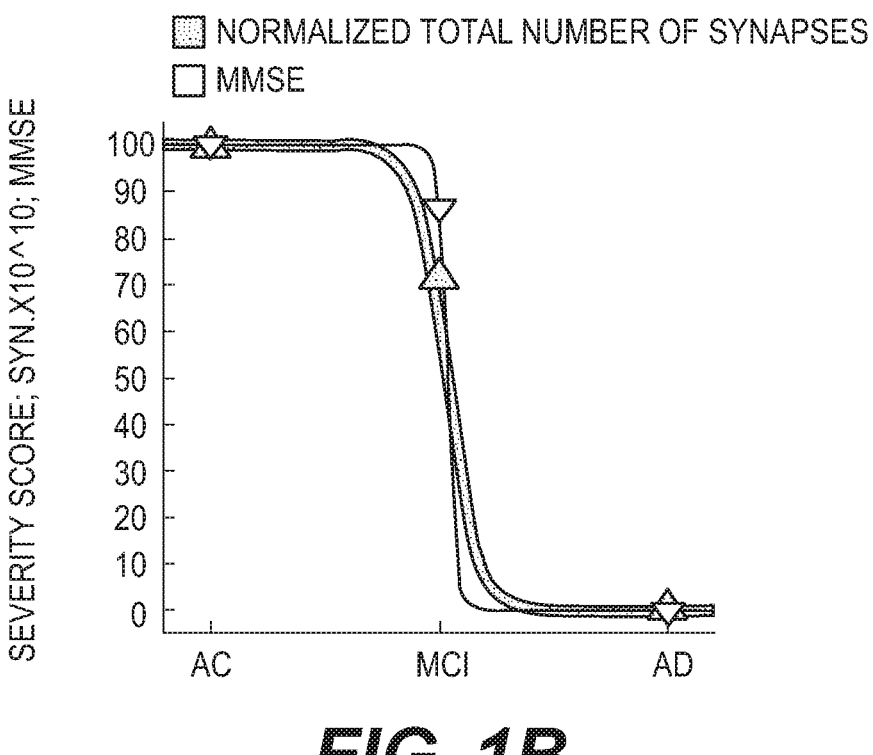

The only pathologic hallmark of the autopsy AD brain that is closely correlated with the extent of cognitive impairment is the loss of synapses. Scheff et al., "Hippocampal synaptic loss in early Alzheimer's disease and mild cognitive impairment," *Neurobiol Aging* 27 (10): 1372-84 (2006); Masliah et al., "Physical basis of cognitive alterations in Alzheimer's disease: synapse loss is the major correlate of cognitive impairment." *Ann Neurol*. Oct; 30 (4): 572-80 (1991). Amyloid plaques are not closely correlated with the degree of cognitive deficits. The total number of synapses, however, are closely correlated with cognitive performance in life. Id. Many patients with impairment of cognition that have not reached the level required for clinical diagnosis of dementia have been classified as having Mild Cognitive Impairment. Scheff et al., *Neurobiol Aging* 27 (10): 1372-84. A significant proportion (approximately 60%) of MCI patients progress to a diagnosis of AD. Many MCI patients have no plaques, but do show a significant loss of synapses that closely correlate with the cognitive deficits (see FIGS. 1A and 1B). Id. Furthermore all three populations, Age-matched Controls (AC), MCI patients, and AD patients show a correlation between the total number of synapses and the results of the MMSE, which is a widely used tool for cognitive screening (see FIGS. 1A and 1B). Id. These collective clinical and pathological findings suggest that the synaptic loss associated with AD has already begun before the onset of AD dementia.

One cause of the Alzheimer's disease synaptic loss is the pathological reduction of synaptogenic PKCε isozymes and their downstream synaptogenic substrates, such as brain-derived neurotrophic factor. Hongpaisan et al., "PKCε Activation Prevents Synaptic Loss, Aβ Elevation, and Cognitive Deficits in Alzheimer's Disease Transgenic Mice," *J. Neuroscience*, 31 (2): 630-643 (2011); Khan et al., "PKCε Deficits in Alzheimer's Disease Brains and Skin Fibroblasts," *Journal of Alzheimer's Disease*, 2015: 43 (2): 491-509. The reduction of PKCα and & occurs in association with elevation of soluble beta amyloid protein (Aβ), but before the appearance of the amyloid plaques or neuronal loss. Id.

Three biomarkers for AD-PKCε Biomarker, AD Index Biomarker, and the Morphometric Imaging Biomarker—are related to synaptic formation, and were found to increase in abnormality as AD progresses. Khan et al., *Journal of Alzheimer's Disease*, 2015: 43 (2): 491-509. All three biomarkers have also been found to correlate with brain changes at autopsy that identifies the AD pathologic diagnosis. The present inventors have developed a Biomarker Severity Score, which corresponds to output signals of a respective biomarker for Age-matched controls (AC) and AD patients. The output signals can, but need not, be normalized, e.g. scaled between 0 and 100%. In one embodiment, the Biomarker Severity Score is represented as a continuous logistic fit function on normalized values (between 0 and 100%) of the output signals for a respective biomarker. The present inventors have discovered that these biomarkers, using the Biomarker Severity Score, can detect the signature of AD before the clinical onset of dementia, such as years before clinical onset, and can be used to diagnose MCI, monitor the progression of MCI, and predict the time to clinical onset of AD dementia. Using the Biomarker Severity Score, the inventors have also discovered methods of screening for a compound useful for treating MCI or for preventing the clinical onset of AD dementia, as well as methods of evaluating or monitoring the therapeutic benefit of an agent for treating MCI or preventing the clinical onset of AD dementia.

In one aspect, a method of diagnosing MCI in a subject comprises:

(a) obtaining one or more cells from the subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker; and (c) comparing the output signal determined in step (b) to output signals of the diagnostic biomarker for AC cells from a group of AC subjects and to output signals of the diagnostic biomarker for AD cells from a group of AD subjects, wherein MCI is indicated in the subject if the output signal determined in step (b) is less than the lowest output signal for the AD cells but greater than the highest output signal for the AC cells.

Figure 5A:
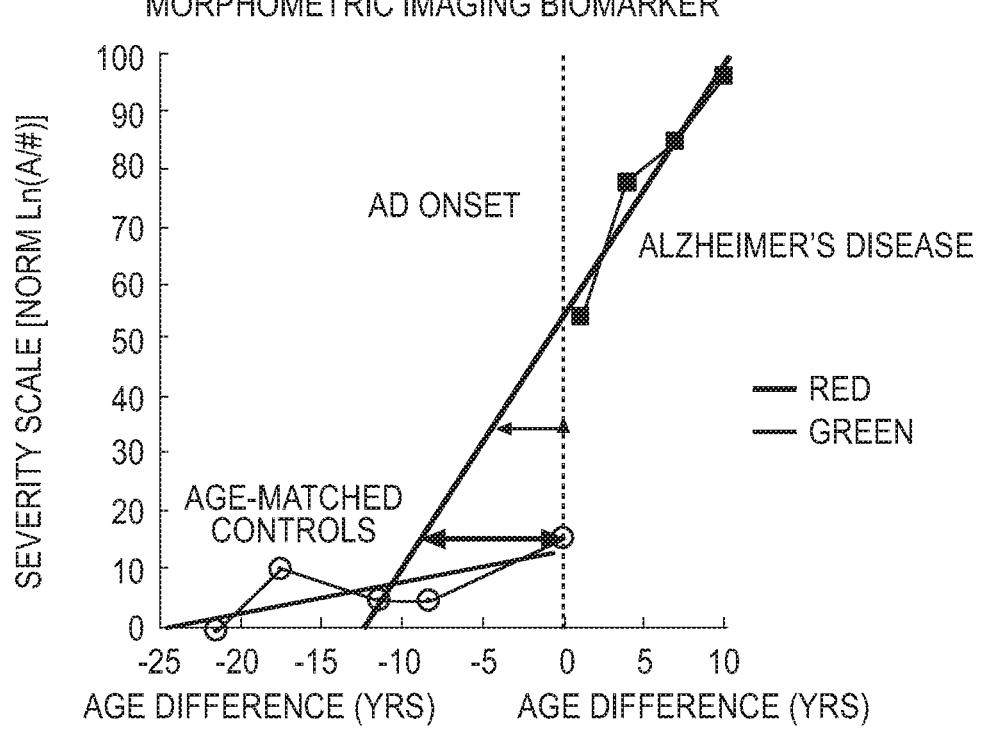
FIG. 5A is similar to FIG. 4A but further illustrates the predictive value of Morphometric Imaging Biomarker applying the linear dependence of the AD group.

The method may further comprise predicting the time to clinical onset of AD dementia, comprising:

(1) plotting the output signals of the diagnostic biomarker for the AD cells as a function of their AD duration, wherein each AD duration is the age difference between the AD subject's age at the time of clinical onset of AD and the AD subject's age at the time of collecting one or more cells for generating the output signals of the diagnostic biomarker:

(2) fitting a function to the plotted output signals of step (1); and (3) if MCI is indicated in step (c), predicting the time to clinical onset of AD dementia by inputting into the fit function the output signal of the diagnostic biomarker determined in step (b) and determining the time to clinical onset of AD dementia. FIGS. 5A and 5B show an example of predicting the time to clinical onset of AD dementia for a hypothetical MCI subject. In some embodiments, the fit function is a linear function.

Alternatively, the method may further comprise predicting the time to clinical onset of AD dementia, comprising:

(1) plotting the output signals of the diagnostic biomarker for the AD cells as a function of their AD duration, wherein each AD duration is the age difference between an AD subject's age at the time of clinical onset of AD and the AD subject's age at the time of collecting one or more cells for generating the output signals of the diagnostic biomarker;

(2) plotting the output signals of the diagnostic biomarker for the AC cells as a function of their age difference, wherein each age difference is the difference between an AC subject's age at the time of collecting one or more cells for generating the output signals of the diagnostic biomarker and the age of the oldest AC subject at the time of collecting one or more cells for generating the output signals of the diagnostic biomarker:

(3) fitting a function to the plotted output signals of steps (1) and (2); and (4) if MCI is indicated in step (c), predicting the time to clinical onset of AD dementia by inputting into the fit function the output signal of the diagnostic biomarker determined in step (b) and determining the time to clinical onset of AD dementia. In some embodiments, the fit function is a logistic function (see FIGS. 6A, 6B, and 6C).

In another aspect, a method of monitoring the progression of MCI comprises repeating steps (a) through (c) above at one or more subsequent points in time, wherein the subject has progressed toward the clinical onset of AD dementia if the output signals determined in step (b) above have increased over time.

In a further aspect, a method of screening for a compound useful for treating MCI or preventing the clinical onset of AD dementia comprises:

(a) obtaining one or more cells from a subject:

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker:

(c) comparing the output signal determined in step (b) to output signals of the diagnostic biomarker for AC cells and for AD cells, wherein MCI is indicated in the subject if the output signal determined in step (b) is less than the lowest output signal for the AD cells but greater than the highest output signal for the AC cells:

(d) if MCI is indicated in step (c), determining the output signal of the diagnostic biomarker in step (b) after contacting cells from the subject with a compound for an initial time period and/or for an ongoing time period; and (e) comparing the output signal determined in step (d) to the output signal determined in step (b), wherein the test compound is indicated as useful for the treatment of MCI or the prevention of the clinical onset of AD dementia if the output signal determined in step (d) is less than the output signal determined in step (b).

The present disclosure also includes a method of screening for a compound useful for treating MCI or preventing the clinical onset of AD dementia, comprising:

(a) obtaining one or more cells from a non-AD, non-demented, non-MCI subject:

(b) contacting the one or more cells with an Aβ peptide:

(c) determining an output signal of one or more diagnostic biomarkers using the one or more cells contacted with the Aβ peptide, wherein the diagnostic biomarker is chosen from AD Index Biomarker, Morphometric Imaging Biomarker and PKC Epsilon Biomarker;

(d) comparing the output signal determined in step (c) to output signals of the diagnostic biomarker for AC cells and for AD cells, wherein MCI is triggered in the subject by step (b) if the output signal determined in step (c) is less than the lowest output signal for the AD cells but greater than the highest output signal for the AC cells;

(e) if MCI is indicated in step (d), determining the output signal of the diagnostic biomarker in step (c) after contacting cells from the subject with a compound for an initial time period and/or for an ongoing time period; and (f) comparing the output signal determined in step (e) to the output signal determined in step (b), wherein the test compound is indicated as useful for the treatment of MCI or the prevention of the clinical onset of AD dementia if the output signal determined in step (d) is less than the output signal determined in step (b).

In another aspect, a method of evaluating or monitoring the therapeutic benefit of an agent for treating MCI or preventing the clinical onset of AD dementia in a subject comprises:

(a) obtaining one or more cells from a subject;

(b) determining an output signal of one or more diagnostic biomarkers using the one or more cells from the subject, wherein the diagnostic biomarker is chosen from AD Index Biomarker, Morphometric Imaging Biomarker and PKC Epsilon Biomarker;

(c) comparing the output signal determined in step (b) to output signals of the diagnostic biomarker for AC cells and for AD cells, wherein MCI is indicated in the subject if the output signal determined in step (b) is less than the lowest output signal for the AD cells but greater than the highest output signal for the AC cells:

(d) if MCI is indicated in step (c), determining the output signal of the diagnostic biomarker in step (b) using one or more cells from the subject after initial, ongoing, and/or cessation of treatment with an agent; and (e) comparing the output signal determined in step (d) to the output signal determined in step (b), wherein the agent is indicated as providing therapeutic benefit for treating MCI or preventing the clinical onset of AD dementia in the subject if the output signal determined in step (d) is equal to or less than the output signal determined in step (b).

The output signals for AC cells and for AD cells as described herein may be determined at or around the same time as determining the output signal for the subject, or the output signals for AC cells and for AD cells may be determined ahead of time, for example, and maintained in a database for comparison to an output signal determined for a given subject.

The AC cells as described herein should be age-matched non-AD, non-MCI cells, i.e., should be obtained from an age-matched non-AD, non-MCI population. In some embodiments, the AC cells are age-matched non-AD, non-demented, non-MCI cells, i.e., should be obtained from an age-matched non-AD, non-demented, non-MCI population.

In some embodiments, the methods described herein are performed using a subject who displays no phenotypic symptoms of AD, such as a subject who displays no phenotypic symptoms of AD, but has one or more risk factors for developing AD.

The output signals of the diagnostic biomarker for AC cells and AD cells that are compared to the output signal of the subject can be average output signals. For example, output signals, as well as the age differences and AD durations as described herein, may be averaged within five-year age intervals resulting in an average output signal and average age difference for each five-year age interval. It will be apparent to those of ordinary skill in the art that other intervals may be applied.

In some embodiments, the cells used to determine the output signals of the biomarkers described herein may be peripheral cells (i.e., cells obtained from non-CNS tissue), including, but not limited to fibroblast cells or blood cells. In some embodiments, the cells are skin fibroblast cells. In other embodiments, the cells are blood lymphocyte cells.

AD Index Biomarker

The "AD Index Biomarker" refers to an assay that measures the change in ratio of a phosphorylated first MAP kinase protein and a phosphorylated second MAP kinase protein when the cells are treated with an agent that is a protein kinase C (PKC) activator. As used herein, determining an output signal of the AD Index Biomarker comprises (i) contacting one or more cells from a subject with an agent that is a PKC activator;

(ii) measuring the ratio of a phosphorylated first MAP kinase protein to a phosphorylated second MAP kinase protein, wherein the phosphorylated first and second MAP kinase proteins are obtained from the cells after the contacting in step (i):

(iii) measuring the ratio of phosphorylated first MAP kinase protein to phosphorylated second MAP kinase protein in one or more cells from the subject that have not been contacted with the agent that is a PKC activator used in step (i); and (iv) subtracting the ratio obtained in step (iii) from the ratio obtained in step (ii).

The phosphorylated MAP kinase proteins may be sequence variants of each other and belong to the same family of proteins. In some embodiments, the phosphorylated first MAP kinase protein is phosphorylated Erk1 and the phosphorylated second MAP kinase protein is phosphorylated Erk2.

The AD Index assay is not limited to the use of any particular PKC activator. In some embodiments, the PKC activator is chosen from bradykinin, bryostatin, bryologs, neristatin, 8-[2-(2-pentyl-cyclopropylmethyl)cyclopropyl]-octanoic acid (DCPLA), and esters of DCPLA. For example, the bryostatin may be chosen from bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. Examples of suitable PKC activators are disclosed in U.S. Patent Publication No. 2014/0315990, which is incorporated herein by reference.

U.S. Pat. No. 7,595,167 and U.S. Patent Application Publication Number 2014/0031245 disclose techniques for carrying out the AD Index assay and are incorporated herein by reference. Thus, the AD Index assay may be performed as described in those publications. For example, in certain embodiments, the PKC activator is bradykinin and the first and second MAP kinase proteins are Erk1 and Erk2, respectively.

Morphometric Imaging Biomarker

The "Morphometric Imaging Biomarker" refers to an assay for measuring cellular aggregation. As used herein, determining an output signal of the Morphometric Imaging Biomarker comprises (i) culturing one or more cells from a subject for a time period sufficient to achieve cell aggregation: (ii) determining the average area of cell aggregates (A) and dividing the average area by the number of aggregates (N) to obtain the average area per number of aggregates (A/N); and (iii) calculating the natural logarithm of (A/N).

The one or more cells may be cultured in a cell media for growth, such as, for example, a protein mixture. In some embodiments, the protein mixture is a gelatinous protein mixture. A non-limiting exemplary gelatinous protein mixture is Matrigel™. Matrigel™ is the trade name for a gelatinous protein mixture secreted by the Engelbreth-Holm-Swarm (EHS) mouse sarcoma cells and marketed by BD Biosciences. This mixture resembles the complex extracellular environment found in many tissues and is used by cell biologists as a substrate for cell culture.

These and other techniques for culturing cells and determining the area and number of aggregates are described in U.S. Pat. No. 8,658,134 and International Patent Publication No. WO2015/103495, which are incorporated herein by reference.

PKC Epsilon Biomarker

The "PKC Epsilon Biomarker" refers to an assay that measures the change in PKCε when the cells are treated with an Aβ peptide. As used herein, determining an output signal of the PKC Epsilon Biomarker comprises (i) determining the PKCε level in one or more cells from a subject: (ii) contacting the one or more cells with an Aβ peptide: (iii) determining the PKC epsilon level in the one or more cells in step (ii) after the contacting step; and (iv) calculating the output signal as the ratio of the slope(S) and intercept (I), (S/I), of the change in PKCε level as a function of Aβ peptide concentration. U.S. Patent Publication No. 2014/0038186 discloses Aβ peptides, contacting cells with an Aβ peptide, and determining PKCε levels and is incorporated herein by reference.

The following examples are provided by way of illustration to further describe certain preferred embodiments of the invention, and are not intended to be limiting of the present disclosure.

Examples

The predictive value of the Biomarker Severity Score was investigated using the AD Index Biomarker, Morphometric Imaging Biomarker, and PKC Epsilon Biomarker. Output signals for the three biomarkers, Ln (A/N), S/I, and $(PERK_1/PERK_2)^{BK+}-(PERK_1/PERK_2)^{BK-}$ for the Morphometric Imaging Biomarker, PKC Epsilon Biomarker, and AD Index Biomarker, respectively, were normalized for two patient populations, AD and AC. The normalized output signals of the biomarkers were shown as a function of the age difference. For the AD group, the age difference was between the age of harvesting for the skin biopsy and the clinical onset of the disease, which was a measure of the disease duration. For the AC group, the current age was subtracted from the oldest age in the AC group and was plotted to the left of the AD onset (dotted vertical line in FIGS. 4A and 4B). The output signals for the PKCε and Morphometric Imaging Biomarkers, as well as the age differences as described herein, were averaged within five-year age intervals resulting in an average output signal and average age difference for each five-year age interval. For the AD Index Biomarker, this average was not necessary because of the abundance of patient data. The output signals for the AC cells were plotted on the left of the disease onset (dotted vertical line in FIGS. 4A and 4B).

Figure 2A:
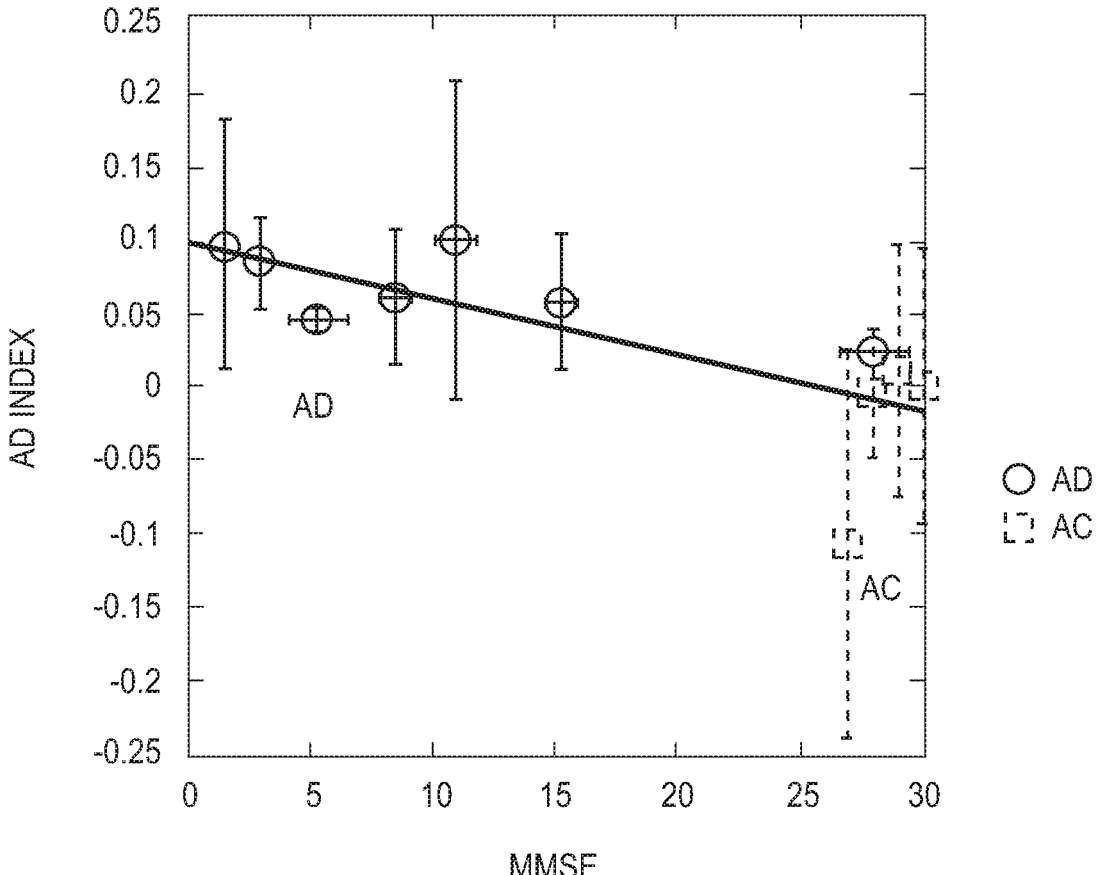
FIG. 2A shows a linear dependence of the AD Index Biomarker on the MMSE score for AC cells (squares) and AD cells (circles).
Figure 2B:
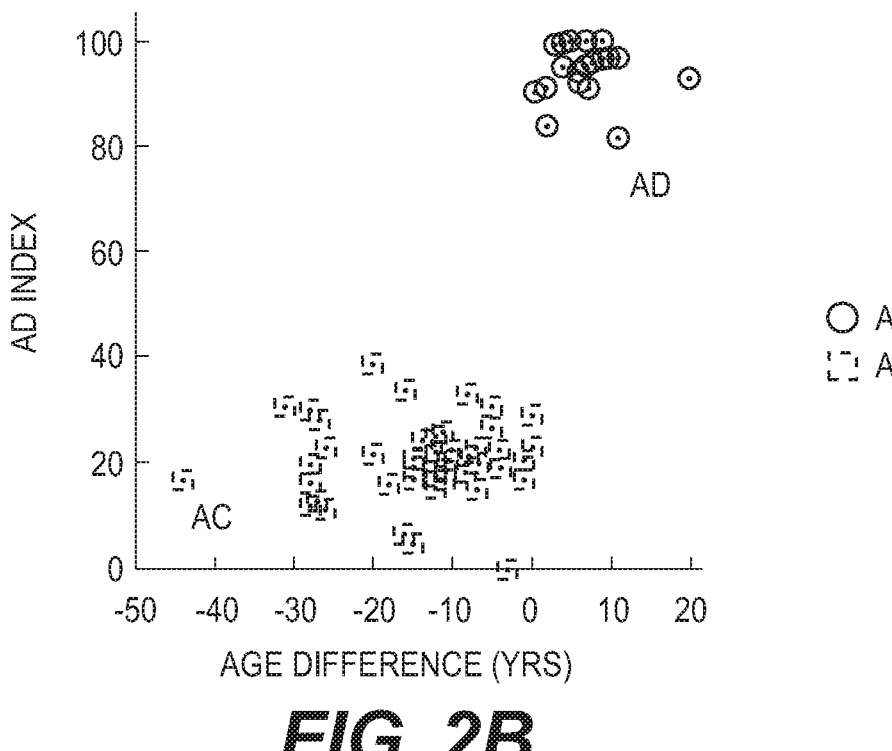
FIG. 2B shows normalized output signals for AC (squares) and AD (circles) cells as a function of AD duration for the AD cells and age difference for the AC cells. AD duration for the AD cells was the age difference between an AD subject's age at the time of clinical onset of AD and the AD subject's age at the time of collecting one or more cells for generating the output signals of the diagnostic biomarker. Age difference for the AC cells was the difference between an AC subject's age at the time of collecting one or more cells for generating the output signals of the diagnostic biomarker and the age at the time of collecting one or more cells for generating the output signals of the diagnostic biomarker of the oldest AC subject in the AC group. The age difference for the AC group was plotted to the left of the AD onset as negative age differences.

The inventors found that the Severity Scores remained constant for AC cells, representing the baseline for the biomarkers. See. e.g., FIGS. 4A and 4B. The Severity Scores also significantly separated the outputs for AC and AD cells, leaving a gap (greater than 40%) in which Biomarker Severity Scores of MCI patients would fall, indicating that each of the biomarkers can detect the signature of AD several years before dementia onset, providing a predictive risk of progression to AD dementia. See. e.g., FIGS. 4A and 4B. In particular, the results provided strong evidence that patients measured with Severity Scores within the separation "gap" will have synaptic loss and MCI that will progress to the stage of AD dementia and its associated pathological hallmarks. It was also found that the Biomarker Severity Scores progressively increased to the time of AD dementia onset (see, e.g., FIGS. 2B, 4A, 4B, 5A, 5B, 6A-6C, 7B, and 8A-8D) and that the Severity Scores remained significantly above baseline at the time of dementia onset (see, e.g., FIGS. 2A and 2B).

Figure 3A:
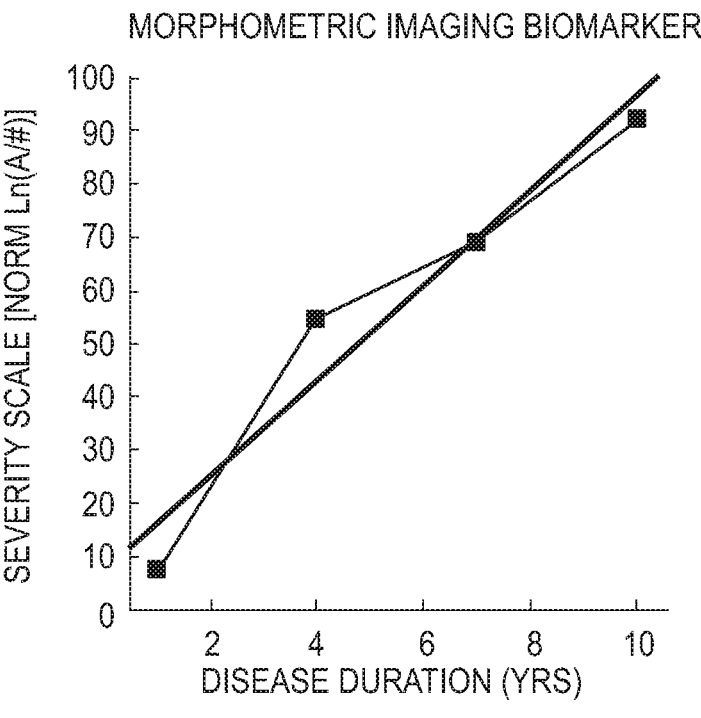
FIGS. 3A and 3 B show Severity Scores for the Morphometric Imaging Biomarker and the PKC Epsilon Biomarker as a function of AD duration.
Figure 3B:
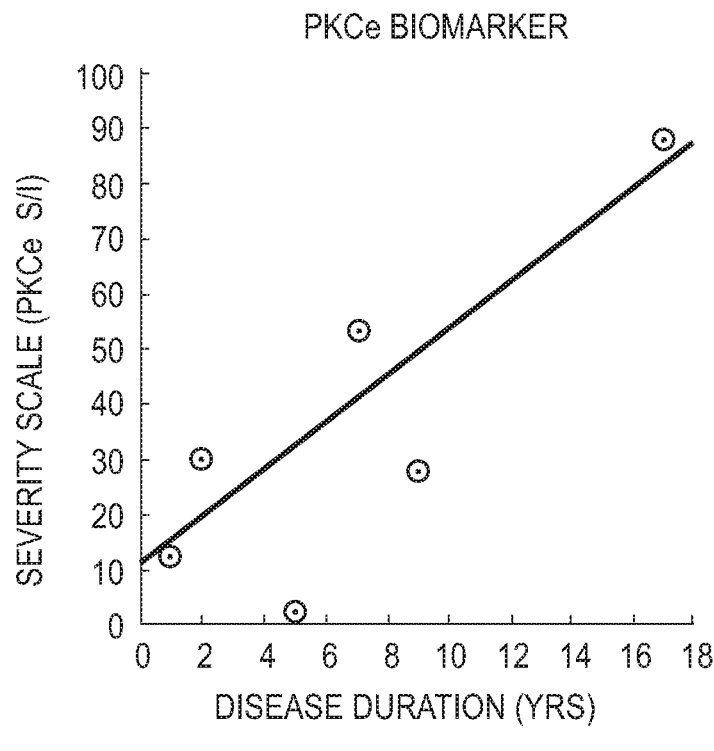
Figure 6C:
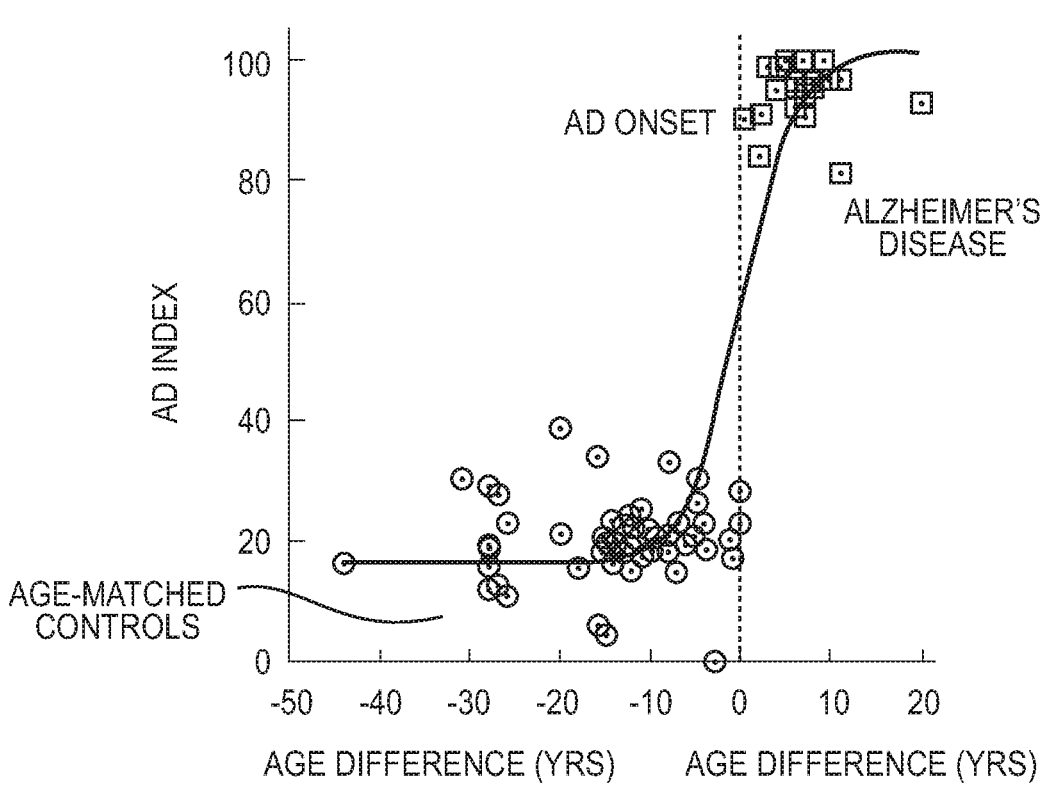

Two out of three biomarkers showed a linear increase of the output signal with the age difference (disease duration) for the AD group (linear fit lines in FIGS. 3A and 3B). The lowest Severity Score for AD was ~12% for the Morphometric Imaging Biomarker and for the PKC Epsilon Biomarker (intersection of linear fit lines with the y axis in FIGS. 3A and 3B). This non-zero value of ~12% for the Severity Score suggests that both biomarkers can detect patients before the onset of dementia. To assess this possibility, the Severity Scores for AC cells were included to access the lowest values of the output signals for the biomarkers (FIGS. 4A, 4B, 5A, and 5B). Due to the normalization procedure in FIGS. 3A and 3B, the maximum signal for the age difference explored was 100%. However, the dependence of the Severity Score on the AD group age difference (disease duration) was expected to saturate for large age differences. Therefore, the linear dependence in the AD group was considered only as a first approximation, and a potentially improved approximation was made as a sigmoidal/logistic function which saturated for large age differences (FIGS. 6A-6C).

The output signals for the AD Index Biomarker were determined as the change in ratio of phosphorylated $ERK_1$ and $ERK_2$ when skin fibroblast cells were treated with bradykinin) (BK+), and were quantified by the difference, $(pERK_1/pERK_2)^{BK+}-(PERK_1/pERK_2)^{BK-}$; as described in Khan et al., "An internally controlled peripheral biomarker for Alzheimer's disease: Erk1 and Erk2 responses to the inflammatory signal bradykinin," *Proc Natl Acad Sci* 29; 103 (35), 13203-7 (2006), and Khan et al., "Early diagnostic accuracy and pathophysiologic relevance of an autopsy-confirmed Alzheimer's disease peripheral biomarker," *Neurobiol Aging,* 31 (6), 889-900 (2010), the methods of which are incorporated herein by reference. See also FIGS. 2A and 2B.

The output signals for the Morphometric Imaging Biomarker were determined by culturing the cells on a thick (1.8 mm) substrate of Matrigel™ for 48 hours and using image analysis software to determine (A/N), as described in Chirila et al., "Spatiotemporal Complexity of Fibroblast Networks Screens for Alzheimer's Disease," *J Alzheimer's Disease* 33, 165-176 (2013) and Chirila et al., "Fibroblast aggregation rate converges with validated peripheral biomarkers for Alzheimer's disease," J Alzheimer's Disease 42, 1279-94 (2014), the methods of which are incorporated herein by reference. See also FIG. 3A.

The output signals for the PKC Epsilon Biomarker were determined by measuring the change in PKCε when the cells were treated with spherical aggregates of β-amyloid Amylospheroids (ASPD), and were quantified by the ratio of the slope(S) and Intercept (I), S/I, as described in Khan et al., "PKCε Deficits in Alzheimer's Disease Brains and Skin Fibroblasts," *Journal of Alzheimer's Disease,* 2015: 43 (2): 491-509, the methods of which are incorporated herein by reference. See also FIG. 3B.

Figure 4A:
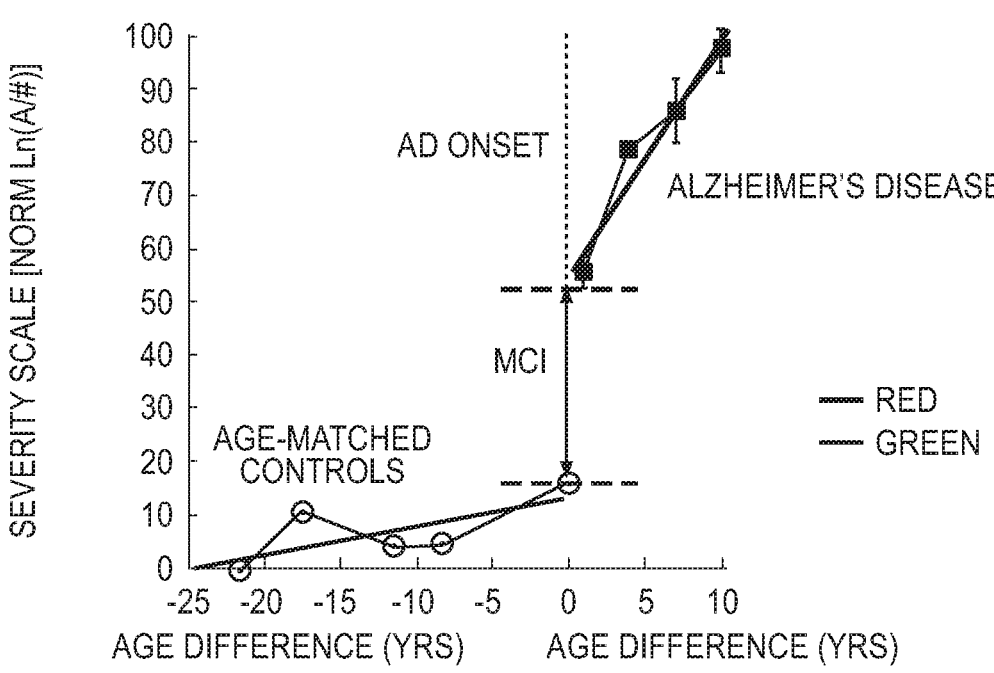
FIG. 4A shows normalized output signals for the Morphometric Imaging Biomarker as a function of AD duration for the AD cells and age difference for the AC cells.
Figure 4B:
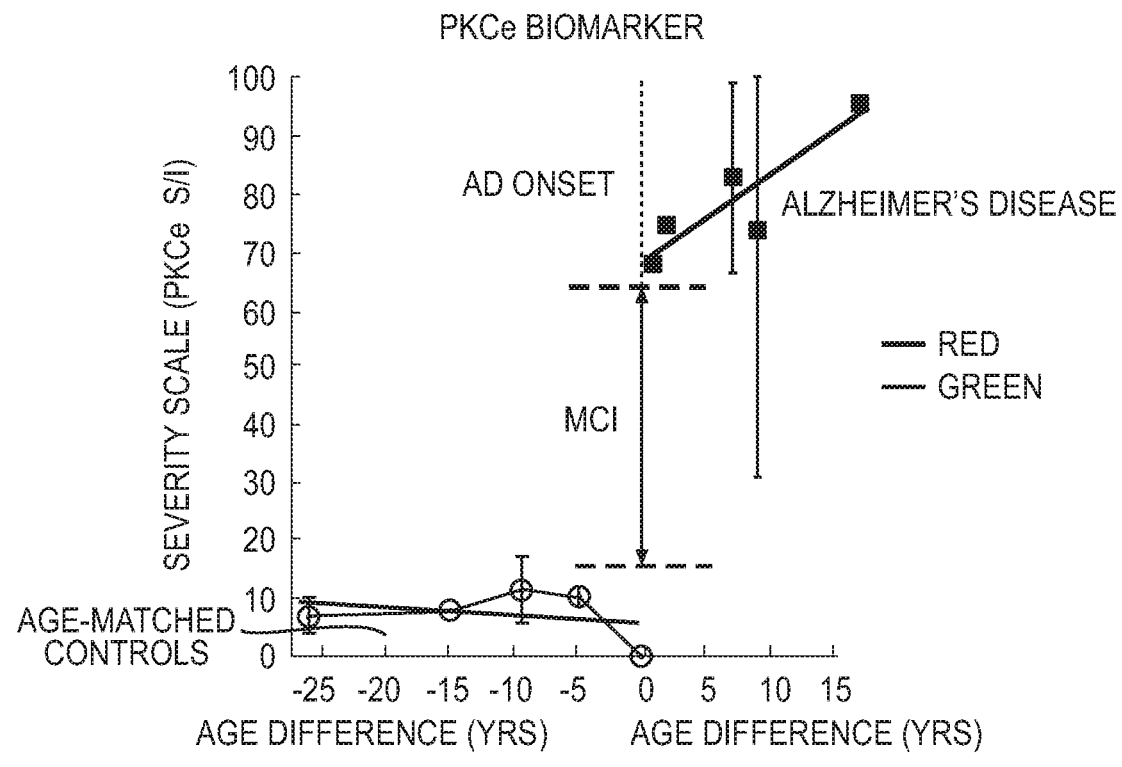
FIG. 4B shows normalized output signals for the PKC Epsilon Biomarker as a function of AD duration for the AD cells and age difference for the AC cells. The age difference for the AC group was plotted to the left of the AD onset line in both figures. The error bars are standard errors of the mean. The vertical arrows indicate the gap between the AC and AD groups. Patients with a Severity Score within this gap are MCI patients.

As shown in FIGS. 4A and 4B, both the Morphometric Imaging Biomarker (FIG. 4A) and the PKC Epsilon Biomarker (FIG. 4B) showed slight changes with the age difference for the AC group as well as a significant gap of >40% between the AC and AD outputs. The Morphometric Imaging Biomarker showed a slight increase with the age difference, while the PKC Epsilon a slight decrease for the AC group (AC fit lines in FIGS. 4A and 4B). The Severity Scores for both biomarkers for the AC group was below 15% and was almost flat for the age differences studied. A saturation toward the lower limit as the age difference became more negative was also expected for the AC group. Therefore, the linear approximation was only a first approximation and a potentially improved approximation was a sigmoidal/logistic function which saturated for the lower limit.

There was a significant signal gap between the AC and AD groups, which were in the normalized form of the Severity Score of ~50% for the PKC Epsilon Biomarker (FIG. 4B) and ~40% for the Morphometric Imaging Biomarker (FIG. 4A)). This gap indicates a population presence identified in clinical studies as MCI patients (see FIGS. 1A and 1B) and shows that these two biomarkers have predictive value. In particular, MCI patients should fill the gap between the AC and AD groups where the signal is greater than 15% and lower than 55% (FIGS. 4A, 4B, 5A, 5B, and 8A-8D).

In a first approximation, it was assumed that MCI patients would follow the same linear trend with age difference as the AD patients (extended AD linear fit line in FIGS. 5A and 5B). The MCI patients would then fill the gap between the AD and AC populations on the left of AD dementia onset (vertical line) (see FIGS. 5A and 5B). The intersection of the extended AD linear fit line with the ~15% Severity Score gave a prediction of the time in advance of clinical onset for which these two biomarkers can detect an MCI patient (lower horizontal arrow in FIGS. 5A and 5B). Under this approach, the Morphometric Imaging Biomarker detected MCI patients ~10 years before clinical onset, while the PKCε biomarker detected patients >27 years before clinical onset. A hypothetical MCI patient (triangle) and predicted time to AD onset (upper horizontal arrow) for the Morphometric Imaging and PKCε Biomarkers are shown in FIGS. 5A and 5B, respectively.

A potentially improved approximation for the location of the MCI patients group was assumed to follow the logistic function (FIGS. 6A-6C). The intersection of the logistic functions with the ~15% Severity Score gave an estimate of the time in advance of the clinical onset for which the biomarkers can detect an MCI patient (horizontal arrows in FIGS. 6A-6C). In this approximation, the Morphometric Imaging Biomarker detected MCI patients ~4 years before the clinical onset (FIG. 6A), while the PKC Epsilon Biomarker detected MCI patients ~5 years before clinical onset (FIG. 6B). Furthermore, the Cut-Off line, which was determined as the intersection of the logistic fit curve with the AD onset vertical line was the same for both of those biomarkers, i.e. ~45%.

The location of the MCI patients were in the gap between AC and AD patients and likely followed a logistic type curve. However, the AC group should be at some distance to the left of the AD onset vertical line. Additionally, the AD group should show an upper limit and therefore a saturation of the signal. These considerations indicate that the predictive value of these two biomarkers should be in between the two applied approximations. Therefore, it was found that the Morphometric Imaging Biomarker should be able to detect MCI patients in between 4 and 10 years while the PKC Epsilon Biomarker should be able to detect MCI patients in between 5 and 25 years.

Figures 7A, 7B:
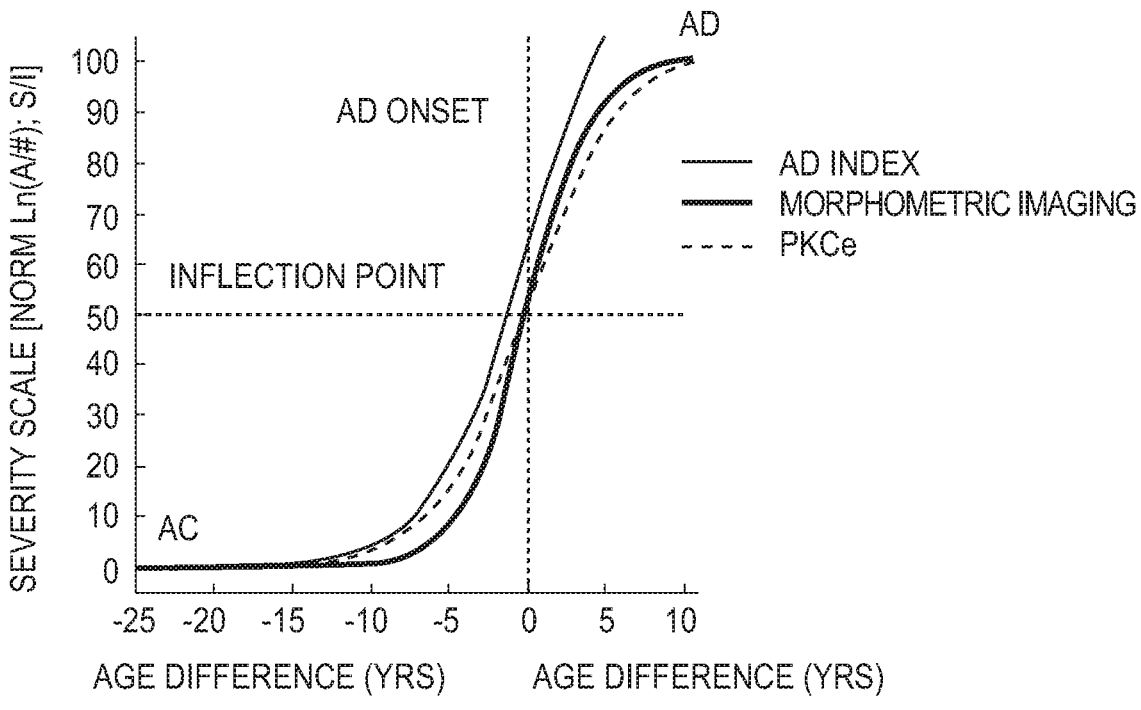
FIG. 7A shows the significant overlap in the Severity Score of the three biomarkers.
FIG. 7B shows the significant overlap for the average for the total number of synapses in the outer molecular layer of the hippocampal dentate gyrus and the average MMSE score for the three populations, AC, MCI, and AD.
Figure 8A:
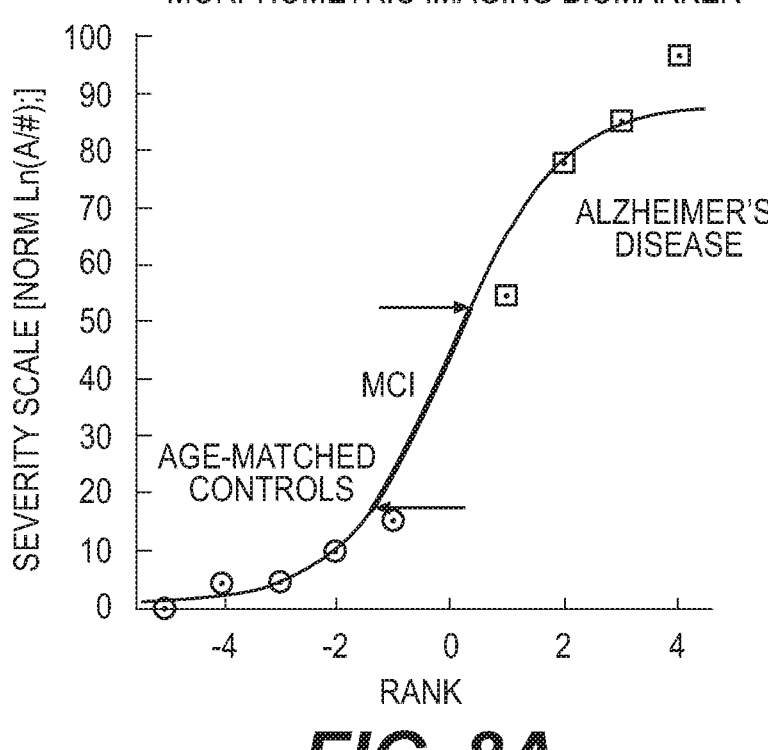
FIGS. 8A, 8B, and 8C shows logistic fit curves for ranked output signals for the Morphometric Imaging, PKC Epsilon, and AD Index Biomarkers, respectively. The MCI patients are located in the gap between the AC and AD groups of patients as indicated by the horizontal arrows and thick lines.
Figure 8B:
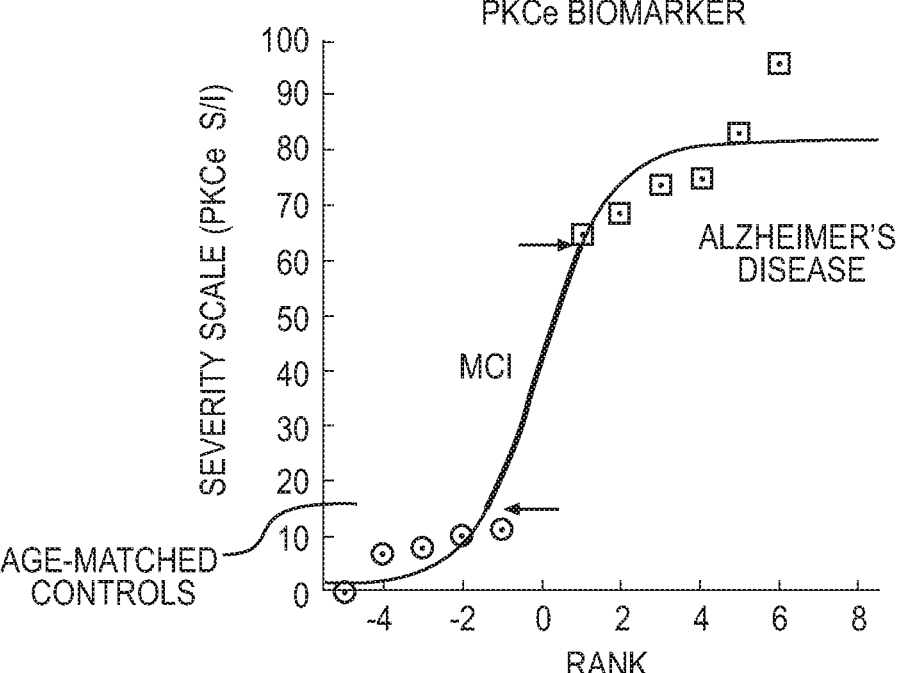
Figure 8C:
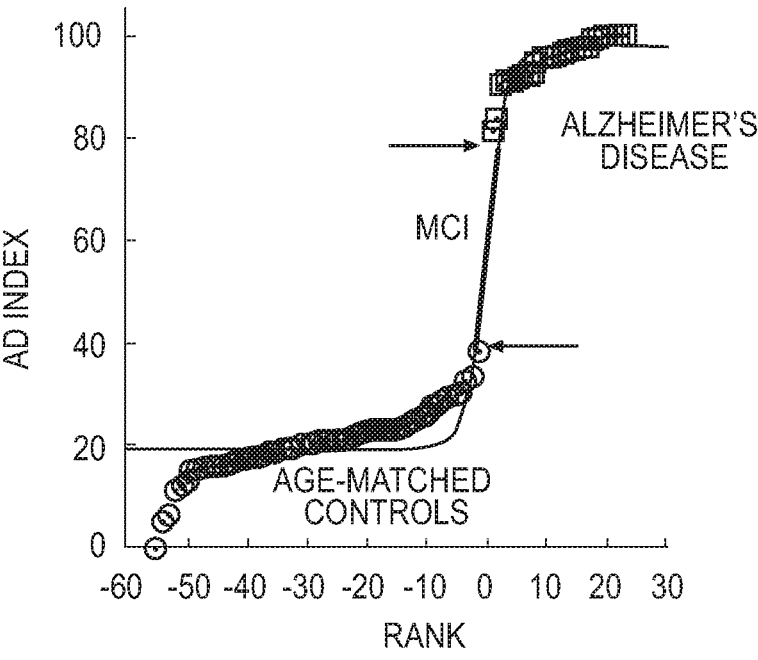
Figure 8D:
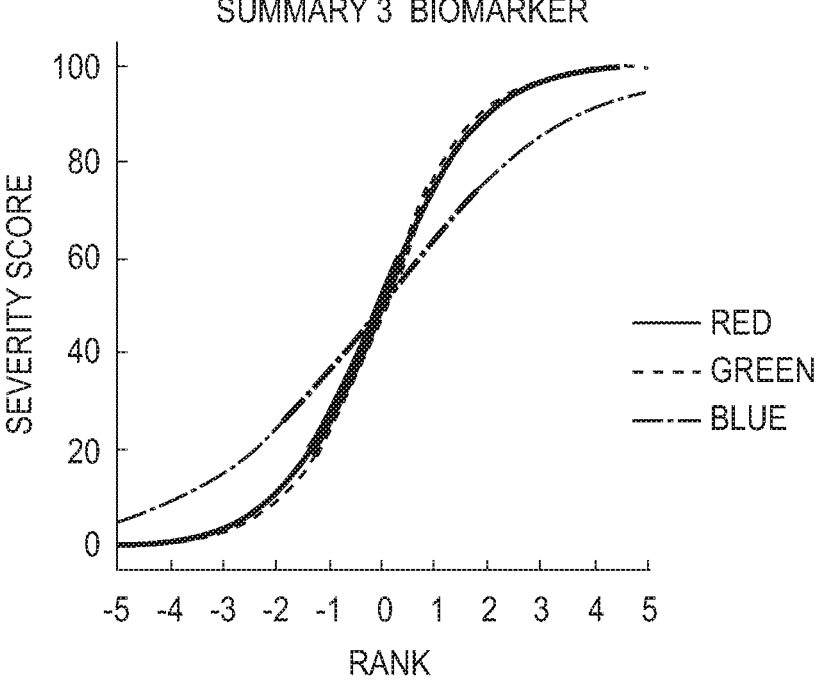
FIG. 8D summarizes FIGS. 8A, 8B, and 8C (Morphometric Imaging-red; PKC Epsilon-green; AD Index-blue).

The remarkable overlap of the biomarkers in their normalized form of the Severity Score is represented by the logistic fit functions in FIG. 7A. The inflection points determined as the intersection between the AD onset line and the logistic curves were practically the same for the Morphometric Imaging and PKC Epsilon Biomarkers. FIG. 7B also shows the significant overlap for the average for the total number of synapses in the outer molecular layer of the hippocampal dentate gyrus and the average MMSE score for the three populations, AC, MCI, and AD. FIGS. 7A and 7B indicate that the three biomarkers track synaptic loss.

The output signals of the three biomarkers were not noise free. Noise can arise from the measurement methods, instruments, or human manipulation. Ranking the output signals of the biomarkers for the AC and AD groups alleviated noise and produced similar results as the "age difference" approach, as shown in FIGS. 8A-8D. The ranking of the output signal for the three biomarkers showed the same gap between the AD and AC groups for the MCI patients and the logistic dependence was more evident in this representation (FIGS. 8A-8D).

All of the references, patents and printed publications mentioned in the instant disclosure are hereby incorporated by reference in their entirety into this application. It should be understood that the foregoing embodiments are examples of the present disclosure and that modifications or alterations may be made therein without departing from the spirit and the scope of the invention as set forth in the appended claims.

What is claimed is:

1. A method for predicting the time to clinical onset of Alzheimer's disease (AD) dementia in a test subject having Mild Cognitive Impairment (MCI) comprising (a) obtaining cells from the test subject;

(b) contacting a first portion of the cells with a Protein Kinase C (PKC) activator while leaving a second portion of the cells uncontacted with the PKC activator, wherein the PKC activator is selected from the group consisting of bradykinin, a bryostatin, a bryolog, neristatin, 8-[2-(2-pentyl-cyclopropylmethyl)cyclopropyl]-octanoic acid (DCPLA), and esters of DCPLA;

(c) determining an output signal of AD Index Biomarker using the cells from the test subject by using levels of phosphorylated extracellular signal-regulated kinase 1 (pERK1) and phosphorylated extracellular signal-regulated kinase 2 (pERK2), wherein the output signal is determined by calculating a first ratio of pERK1 to pERK2 in the first portion of the cells, calculating a second ratio of pERK1 to pERK2 in the second portion of the cells, and subtracting the second ratio from the first ratio to obtain the output signal of AD Index Biomarker;

(d) obtaining a graph of AD Index Biomarker values, the graph having plotted thereon:

first AD Index Biomarker values for cells obtained from AD-afflicted subjects and second AD Index Biomarker values for cells obtained from age-matched control subjects, wherein the graph has as its x-axis age difference in years and has as its y-axis AD Index values from 0-100, the graph includes an inflection point between the first AD Index Biomarker values and the second AD Index Biomarker values; and the first AD Index Biomarker values and the second AD Index Biomarker values are obtained using levels of pERK1 and pERK2 in the cells obtained from AD-afflicted subjects and in the cells obtained from the age-matched control subjects, respectively; and (e) plotting the output signal determined in step (c) on the graph obtained in step (d), and predicting the time to clinical onset of AD dementia in the test subject based on the position of the output signal determined in step (c) on the graph relative to the inflection point, wherein the age difference for each AD-afflicted subject is the difference in age between the time of clinical onset of AD and the age at the time of collecting cells, and the age difference for each age-matched control subject is the difference in age between the age at the time of collecting cells from the age-matched control subject and the age of the oldest age-matched control subject at the time of collecting cells from that subject.

2. The method of claim 1, wherein the PKC activator is bradykinin.

3. The method of claim 1, further comprising monitoring the progression of MCI, comprising repeating steps (a) through (e) at one or more subsequent points in time, wherein the subject has progressed toward the clinical onset of AD dementia if the output signals determined in step (c) have increased over time.

4. The method of claim 1, wherein the cells are peripheral cells.

5. The method of claim 4, wherein the peripheral cells are skin fibroblast cells.

6. The method of claim 1, wherein the test subject displays no phenotypic symptoms of AD.

7. The method of claim 1, wherein the method further comprises determining an output signal of a Morphometric Imaging Biomarker using the cells from the test subject, wherein determining the output signal of the Morphometric Imaging Biomarker comprises:

(i) culturing one or more cells from the test subject for a time period sufficient to achieve cell aggregation;

(ii) determining the average area of cell aggregates (A) and dividing the average area by the number of aggregates (N) to obtain the average area per number of aggregates (A/N); and (iii) calculating the natural logarithm of (A/N).

8. The method of claim 1, wherein the method further comprises determining an output signal of a PKC Epsilon Biomarker using the cells from the test subject, wherein determining the output signal of the PKC Epsilon Biomarker comprises:

(i) determining the PKC level in one or more cells from the test subject;

(ii) contacting the one or more cells with an Aβ peptide;

(iii) determining the PKC epsilon level in the one or more cells in step (ii) after the contacting step; and (iv) calculating the output signal as the ratio of the slope(S) and intercept (I), (S/I), of the change in PKCε level as a function of Aβ peptide concentration.

9. The method of claim 1, wherein the PKC activator is a bryostatin selected from the group consisting of bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, and bryostatin-18.

* * * * *